United States Patent
Ju

(10) Patent No.: US 9,062,329 B2
(45) Date of Patent: Jun. 23, 2015

(54) PRODUCTION OF ARABITAL

(75) Inventor: Lu-Kwang Ju, Akron, OH (US)

(73) Assignee: The University of Akron, Akron, OH (US)

( * ) Notice: Subject to any disclaimer, the term of this patent is extended or adjusted under 35 U.S.C. 154(b) by 25 days.

(21) Appl. No.: 13/811,298

(22) PCT Filed: Jul. 22, 2011

(86) PCT No.: PCT/US2011/001302
§ 371 (c)(1),
(2), (4) Date: Jan. 21, 2013

(87) PCT Pub. No.: WO2012/011962
PCT Pub. Date: Jan. 26, 2012

(65) Prior Publication Data
US 2013/0116475 A1     May 9, 2013

Related U.S. Application Data

(60) Provisional application No. 61/366,979, filed on Jul. 23, 2010.

(51) Int. Cl.
*C07C 31/18* (2006.01)
*C12P 7/18* (2006.01)
*C12P 7/20* (2006.01)
*C12N 1/00* (2006.01)

(52) U.S. Cl.
CPC . *C12P 7/18* (2013.01); *C07C 31/18* (2013.01); *C12P 7/20* (2013.01)

(58) Field of Classification Search
CPC ............. C07C 31/18; C12P 7/20; C12P 7/18
USPC ............... 568/852; 435/158, 159, 243, 255.1, 435/255.21, 255.7, 256.8
See application file for complete search history.

(56) References Cited

U.S. PATENT DOCUMENTS

| 2,793,981 | A | 5/1957 | Spencer et al. |
| 2,934,474 | A | 4/1960 | Owen et al. |
| 3,607,652 | A | 9/1971 | Ueda |
| 6,268,190 | B1 * | 7/2001 | Duflot et al. ................. 435/158 |

FOREIGN PATENT DOCUMENTS

JP    2009/148211    7/2009

OTHER PUBLICATIONS

Girio et al., Polyols production during single and mixed substrate fermentations in *Debaryomyces hansenii*. Bioresource Technology. 71: 245-251, 2000.*
Zhu et al., Production of D-arabitol by a newly isolated *Kodamaea ohmeri*. Bioprocess Biosyst Eng. 33:565-571, Published online: Sep. 19, 2009.*
Nozaki et al., Production of D-Arabitol by *Metschnikowia reukaufii* AJI4787. Biosci. Bitechnol. Biochem. 67 (9), 1923-1929. 2003.*
Carvalheiro et al., Xylitol production by *Debaryomyces hansenii* in brewery spent grain dilute-acid hydrolysate: effect of supplementation. Biotechnol Lett. 29:1887-1891, 2007.*
International Search Report; Feb. 27, 2012.
Girio et al; Polyols production during single and mixed substrate fermentations in *Debaryomyces hansenii*; Bioresource Technology 71; 2000; 245-251.
Zhu et al; Production of d-arabitol by a newly isolated *Kodamaea ohmeri*; Bioprocess Biosyst Eng 2010; Sep. 19, 2009; 33:565-571.
Saha et al; Production of d-arabitol by a newly isolated *Zygosaccharomyces rouxii*; J Ind Microbiol Biotechnol; 2007; 34:519-523.

* cited by examiner

*Primary Examiner* — Ganapathirama Raghu
(74) *Attorney, Agent, or Firm* — Renner Kenner Greive Bobak Taylor & Weber

(57) ABSTRACT

A method for producing arabitol, and more particularly to producing arabitol in a major amount based on a total weight of all polyols produced and in relatively high concentration from a mixture including a carbon source such as glycerol. The method includes in one embodiment utilizing select yeast strains to produce arabitol in high yield while minimizing the amounts of other polyols, using carbon sources such as glycerol as a component in a medium. In a beneficial embodiment, biodiesel byproduct glycerol is used as the substrate for arabitol production.

13 Claims, 8 Drawing Sheets

PRODUCTION OF ARABITAL

CROSS-REFERENCE

This Application claims the benefit of priority under 35 U.S.C. §119 of U.S. Provisional Application Ser. No. 61/366,979, filed on Jul. 23, 2010, herein fully incorporated by reference.

FIELD OF THE INVENTION

The present invention relates to methods for producing arabitol in a major amount based on a total weight of all polyols produced and in relatively high concentration, and more particularly to producing arabitol from a mixture including a carbon source such as glycerol. The method includes in one embodiment utilizing select yeast strains to produce arabitol in high yield while minimizing the amounts of other polyols, using carbon sources such as glycerol as a component in a medium. In a beneficial embodiment, biodiesel byproduct glycerol is used as the substrate for arabitol production.

BACKGROUND OF THE INVENTION

Biodiesel produced from renewable sources like vegetable oils and animal fat is an attractive alternative fuel (Krawczyk 1996). In biodiesel production using transesterification of triglycerides, glycerol is the major byproduct produced; about 1 kg of glycerol is formed for every 9 kg of biodiesel produced (Dasari et al. 2005). Biodiesel consumption in the United States has increased dramatically from 75 million gallons in 2005 to 700 million gallons in 2008. The latter resulted in the production of around 50 million gallons of glycerol (http://biodiesel.orgiresources/faqs/, (Dasari 2007)). Refined glycerol has numerous applications in food, drug, textile and cosmetic industries whereas crude glycerol produced from biodiesel industry is of low value because of its impurities like spent catalyst, salts after neutralization, residual methanol, methyl esters and free fatty acids (Liu et al. 2002; Boumay et al. 2005). The economies of biodiesel industry is strongly influenced by the value of its byproducts. Developing new uses of biodiesel glycerol is imperative to economics and sustainability of the biodiesel industry (Demirbas 2003; Haas et al. 2006).

Arabitol is a polyhydric alcohol that can be used as a low calorie sweetener (Huck et al. 2004). In addition, a study by the Department of Energy identified arabitol, and its enantiomer xylitol, as ode of the top twelve biomass-derivable building block chemicals. Arabitol and xylitol can be transformed into several groups of chemicals like xylaric/xylonic acid, arabonic/arabinoic acid, propylene glycol and ethylene glycol (Werpy and Petersen 2004). Arabitol and xylitol have melting points of 103° C. and 93° C., respectively. Both are highly soluble in water and both form white crystals when purified (Le Toumeau 1966; Talja and Roos 2001). The catabolism of arabitol by *Escherichia coli* involves the formation of arabitol phosphate which induces the synthesis of compounds that inhibit the bacterial metabolism (Scangos and Reiner 1979). While more studies are required, the above property makes it possible to use arabitol as sweetener for reducing dental canes. Also, the caloric value of arabitol is 0.2 kcal/g whereas it is 2.4 kcal/g for xylitol, it is highly possible that arabitol can be used in many of the known applications of xylitol, as a natural sweetener, a dental caries reducer and a sugar substitute for diabetic patients (Gare 2003). If desirable, arabitol can also be converted to xylitol, for example, by using *Glucanobacter oxydans* (Suzuki et al. 2002). This bacterium was capable of oxidizing D-arabitol to D-xylulose using the membrane-bound D-arabitol dehydrogenase and then converting D-xylulose to D-xylitol using the also membrane-bound D-xylitol dehydrogenase. Xylitol yield of around 25% has been reported (Sugiyama et al. 2003).

Xylitol is currently produced in one embodiment by chemical reduction of xylose derived from wood hydrolysate under alkaline conditions (Melaja and Hamalainen 1977). This process requires high pressure (50 atm) and temperature (80-140° C.) and uses relatively expensive catalyst and relatively extensive separation steps. Xylitol production from xylose by biological processes has also been explored (Leathers et al. 2000; Kim et al. 2002; Kastner et al, 2003; Buhner and Agblevor 2004). Yeast can covert xylose to xylitol using NAD(P)H-coupled xylose reductase. Unfortunately, the xylitol produced tends to be oxidized to xylulose by $NAD^+$-coupled xylitol dehydrogenase. Good xylitol yields from such a process require tightly controlled, high intracellular $NAD(P)H/NAD^+$ ratios. This control is not an easy task in large-scale industrial operations where the environment (particularly the dissolved oxygen concentrations) inside the large bioreactors is not homogeneous. The above chemical and biological processes require costly separation of xylose from the complex sugar mixtures in the biomass hydrolysate. The alternative approach of producing arabitol from biodiesel glycerol and then, if desirable, converting arabitol to xylitol may prove economically attractive. Arabitol is known to be produced by osmophilic yeast species such as *Debaryomyces Candida* (Bernard et al. 1981), *Pichia* (Bisping et al. 1996), *Hansenula* (Van Eck et al. 1989) and *Endomycopsis* (Hajny 1964). When exposed to osmotic stress, the yeast accumulates compatible solutes such as arabitol, glycerol, xylitol, erythritol and mannitol to balance the osmotic pressure across the cell membrane.

U.S. Pat. No. 2,793,981 relates to the production of polyhydric alcohols. More particularly it relates to the simultaneous formation of glycerol and D-arabitol by fermentation of a sugar.

U.S. Pat. No. 2,934,474 relates to the production of polyhydric alcohols, and in particular to the production of D-arabitol, by fermentation.

U.S. Pat. No. 3,607,652 relates to a process for the fermentative production of D-arabitol by cultivating under aerobic condition a micro-organism *Pichia ohmeri* No. 230 (ATCC Deposit No. 20209) in a nutrient medium containing fermentable saccharides such as glucose, sucrose, mannose, fructose and the like as carbon source, and recovering D-arabitol accumulated in the cultivated liquor. D-arabitol is reportedly obtained at a high yield without substantial formation of other polyhydric alcohols having similar properties.

U.S. Pat. No. 4,271,268 relates to the preparation of D-arabitol by a fermentative process utilizing a micro-organism of the species *Pichia haplophila* or mutants thereof in a nutrient medium containing as a carbon source a hydrocarbon or ethyl alcohol.

U.S. Pat. No. 5,846,794 relates to a process for the preparation of D-arabitol, characterised in that it comprises the following stages: hydrolysis of a lactose solution, oxidation of the mixture of glucose and galactose thus obtained to a mixture of gluconic and galactonic acids, decarboxylation of this mixture of gluconic and galactonic acids to a mixture of D-arabinose and D-lyxose, catalytic hydrogenation of this mixture of D-arabinose and D-lyxose to D-arabitol.

Production of D-arabitol by a Newly Isolated *Kodamsea ohmeri*, in Bioprocess Biosyst Eng (2010) 33:565-571, reports production of arabitol from glucose using a specific strain. The work was done in shake flasks without pH and DO (dissolved oxygen concentration) control. The species produces glycerol and ethanol as the byproducts, with 8 and 20 g/L concentration respectively.

In view of the above, it would be desirable to provide a method for the production of arabitol, using biological fermentation agents and processes.

SUMMARY OF THE INVENTION

It is an object of the present invention to provide methods for arabitol production utilizing microorganisms, preferably with relatively high yields or concentrations.

Yet another object is to provide a method that produces arabitol using relatively mild reaction conditions.

Still another object is to provide methods for making arabitol that produce relatively minimal or minor percentages of other reaction products such as other polyols.

A further object of the invention is to provide a method including the steps of combining components to form a medium mixture comprising water, a carbon source such as glycerol, glucose and/or xylose, a yeast; and other nutrients that promote cell growth, for example peptone and malt; and producing arabitol from the medium mixture.

An additional object of the present invention is to produce arabitol utilizing a relatively economical process.

An additional object is to provide methods for producing arabitol via fermentation utilizing one or more of *Debaryomyces, Geotrichum,* and *Metschnikowia* yeast genera with the *Debaryomyces* and *Metschnikowia* genera being most preferred, wherein in one embodiment at least glycerol is used as a carbon source in the medium, and in a further embodiment glucose and xylose are utilized as a carbon source.

Accordingly, in one aspect of the present invention a process for producing arabitol is disclosed, comprising the steps of combining a carbon source with a yeast in a medium, and producing a major amount of the arabitol based on a total weight of all polyols produced by the process, and wherein the arabitol is produced in an amount greater than 30 g/L of the medium and at least 40% conversion of the carbon source consumed, that is, at least 4 g of arabitol is produced per 10 g of carbon source consumed.

In another aspect, an arabitol mixture is disclosed, comprising a major amount of arabitol based on a total weight of all polyols in the mixture, produced by combining a carbon source with a yeast in a medium, and wherein the arabitol is present in an amount greater than 30 g/L of the medium.

DETAILED DESCRIPTION OF THE INVENTION

Figure 1:
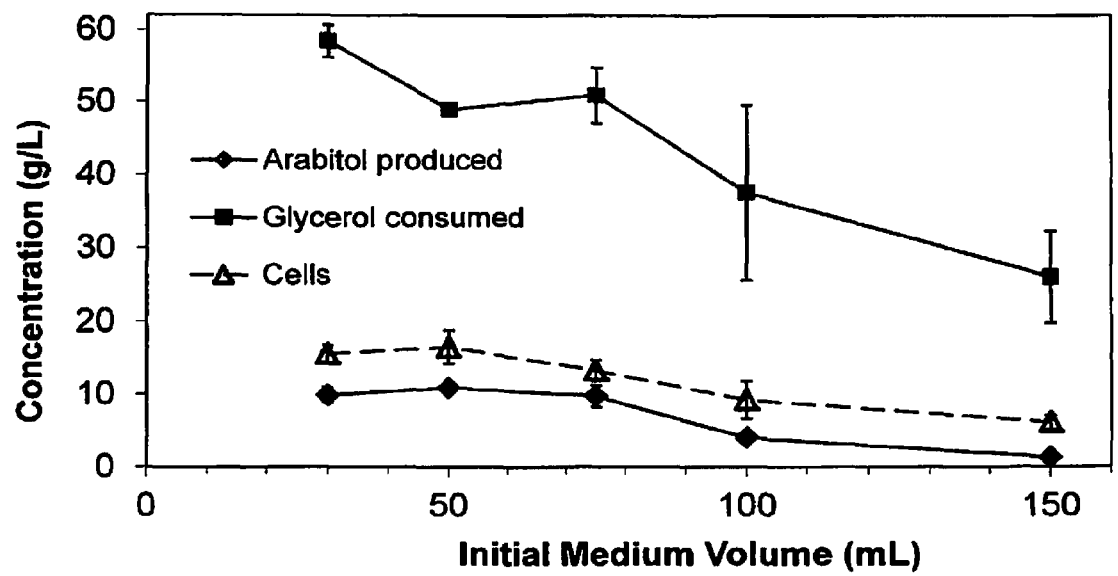
FIG. 1 is a graph illustrating concentrations of arabitol produced, glycerol consumed and cells grown in the systems with different initial culture volumes, wherein arabitol and glycerol concentrations were measured at 120 h and cell concentrations were measured at 80 h.

The polyhydric or sugar alcohol arabitol is produced with the methods of the present invention by utilizing microorganisms, m particular a yeast, preferably of the genera *Debaryomyces, Geotrichum* and *Metschnikowia,* and more preferably *Debaryomyces* and *Metschnikowia,* utilizing in the medium a carbon source such as one or more of glycerol and a hydrolysate of plant biomass, such as one or more of glucose and xylose. Among other uses such as intermediates, arabitol can be used as a low calorie sweetener.

The microorganisms used to produce the arabitol are yeasts of genera *Debaryomyces, Metschnikowia* and *Geotrichum*. Preferably yeast of the genera *Debaryomyces* and *Metchnikowia* are utilized as such strains have been discovered to produce predominantly arabitol, based on total polyol content when glycerol is used as a substrate. The *Geotrichum* strains while producing a major amount of arabitol, have also been found to produce minor amounts of other polyols such as mannitol. Regarding the *Debaryomyces* genera, a suitable species or strain thereof is *D. hansenii.* Regarding yeast of the genera *Metschnikowia*, a suitable species or strain is *M. zobellii.* Regarding the *Geotrichum* genera, suitable species or strains thereof are *G. candidum, G. fermentans* and *G. cucujoidarum,* with *G. candidum* and *G. cucujoidarum* being preferred. Various strains of microorganisms can be obtained from the Northern Regional Research Laboratories (NRRL) Culture Collection of United States Department of Agriculture's Research Service. The concentration of the yeast utilized in the initial medium mixture ranges generally torn about 0.05 to about 5 g/L, desirably from about 0.1 to about 3 g/L and preferably from about 0.5 to about 2 g/L of medium. The maximum concentration of the yeast reached by growth in the process ranges generally from about 5 to about 60 g/L, desirably from about 10 to about 50 g/L and preferably from about 20 to about 40 g/L of medium. Water is preferably utilized as the basis for medium.

The processes according to the invention are carried out by growing or otherwise cultivating the microorganisms, i.e. yeasts, used to produce the arabitol, in a liquid medium mixture which includes but is not limited to, one or more of a carbon source, nitrogen source and a nutrient such as an organic or inorganic nutrient, a vitamin, an amino acid and the like. In a preferred embodiment the liquid medium mixture includes at least a yeast a carbon source, and a nitrogen source.

The glycerol used as a carbon source to prepare the arabitol can be from any desirable source. In one preferred embodiment, the glycerol is obtained as a byproduct of biodiesel production. The initial concentration of glycerol in the growing medium ranges generally from 50 g/L to about 400 g/L, desirably from about 80 to about 200 g/L and preferably from 100 to about 130 g/L of the medium.

One or more additional carbon sources can be utilized with or instead of the glycerol in some embodiments, for example glucose, xylose and a hydrolysate of lignocellulosic biomass. Other optional carbon sources that could be used are sucrose, arabinose and xylulose. When utilised with the glycerol, such amounts of other carbon sources are preferably less than the amounts of glycerol utilized in one embodiment. In one embodiment where glycerol is utilized in combination with glucose and xylose, independently, the initial glucose concentration can range from about 30 to about 200 g/L and the initial xylose concentration can range from about 30 to about 150 g/L. In a preferred embodiment, a medium mixture including glycerol is preferably free of sorbitol, which has been found to reduce the arabitol production.

In a further embodiment, the carbon source is a combination of glucose and xylose and optionally other suitable substrates such as the less abundant sugars present in hydrolysate prepared from lignocellulosic biomass. In such an embodiment, the initial concentration of the glucose ranges from about 30 to about 400 g/L, generally from about 80 to about 300 g/L and desirably from about 100 to about 200 g/L of the medium, and the initial concentration of the xylose ranges from about 30 to about 200 g/L, generally from about 80 to about 150 g/L and desirably from about 60 to about 100 g/L of the medium.

In one embodiment, the medium utilizes a nitrogen source for example peptone, yeast extract, malt extract, ammonium sulfate, ammonium nitrate, and urea. In addition to serving as a nitrogen source, peptone, yeast extract and malt extract act as a source of carbohydrates, proteins, mono-, di- and oligo-saccharides. Suitable initial amounts of the nitrogen sources can be utilized, for example the yeast extract can range in an amount, from about 3 to about 30 g/L, ammonium sulfate in an amount from about 2 to about 20 g/L, peptone in an amount from about 3 to about 30 g/L and malt extract in an amount from about 3 to about 50 g/L of the medium.

The medium can also include in one embodiment a phosphate source, such as potassium phosphate, such as monobasic potassium phosphate or dibasic potassium phosphate for the cell growth and product production. In general, initial monobasic and dibasic potassium phosphate concentrations used are in the range of about 1 to about 12 g/L of medium.

The production of arabitol is carried out under aerobic conditions in one embodiment preferably by agitating and/or aerating the medium utilizing any suitable device such as a mixer, agitator, compressed air, compressed oxygen, air/oxygen sparging orifice, air/oxygen diffuser, etc. The process requires a sufficient concentration of dissolved oxygen in order to provide cell growth and arabitol formation. In one embodiment, dissolved oxygen concentration is at least 2 percent of air saturation (that is, about 0.15 mg of dissolved oxygen per L of medium) and is desirably about 5% to 10% (that is, about 0.4 to 0.8 mg/L).

Different concentrations of arabitol are produced at different temperatures by the yeasts utilized in the present invention. In general, the process temperature is in the range between about 20° C. to about 50° C. and desirably from about 28° C. to about 30° C. and preferably is about 30° C. Considering specific yeast microorganisms, *D. hansenii* strains are generally maintained in a temperature range from about 20° C. to about 35° C. and preferably from about 25° C. to about 30° C.; *G. candidum* strains are maintained in a temperature range from about 20° C. to about 35° C. and preferably from about 25° C. to about 30C; *G. cucujoidarum* strains are maintained in a temperature range from about 20° C. to about 35° C. and preferably from about 25° C. to about 30° C.; *M. zobellii* strains are maintained in a temperature range from about 25° C. to about 30° C. and preferably from about 25° C. to about 30° C.

Suitable pH for the medium mixture is generally from about 3 to about 6 and preferably from about 3 to about 4.

In view of the above, in one embodiment the process of the present invention comprises the steps of combining a desired concentration of a carbon source, at least glycerol in a preferred embodiment, and one or more selected yeast microorganisms, as well as any other desired components; and forming a mixture in a medium; and producing arabitol from the mixture, preferably utilizing the conditions described herein. In one embodiment, the glycerol and/or other carbon sources and any other desired components besides the yeast are autoclaved at a suitable temperature separately from the other medium components prior to mixing in order to destroy undesirable biological agents (such as organisms and spores) or otherwise sterilize the non-yeast components to be used in the fermentation.

Depending upon the yeast strain used, other polyol products may be produced. The fermentation, process is continued until a suitable amount of arabitol is produced as desired. The process time can range depending upon factors such as the yeast microorganisms utilized and can range from about 2 to about 10 days and preferably from about 3 to about 6 days. The process produces arabitol in an amount generally greater than 80 parts by weight based on 100 total parts by weight of polyol produced by the process, desirably greater than 70, 80 or 00 parts by weight and preferably greater than 9:2 or 95 parts by weight. The presence and concentration of arabitol and other polyols can be measured using HPLC in a preferred embodiment. An important benefit of the processes of the present invention is that large amounts of arabitol are produced per liter of medium. When glycerol is utilized as a carbon source, alone or in combination with a total minor amount of other carbon sources, at least 35 grams, and desirably at least 50 grams of arabitol are produced per liter of medium. The processes of the invention produce arabitol in at least 40%, desirably at least 50% and preferably at least 60% conversion of the carbon source consumed. That is, for an at least 40% conversion, at least 4 g of arabitol is produced per 10 g of carbon source consumed. In one embodiment where glucose and xylose are utilized as a carbon source mixture, arabitol is produced in an amount of at least 30 g/L of the medium and desirably greater than 34 g/L of medium per 80 g/L of glucose and xylose consumed.

EXAMPLES

Yeast Strain Screening

Extensive culture screening of 214 strains from 25 genera was conducted for arabitol production from glycerol. The following 5 genera contained the largest numbers of strains screened: *Debaryomyces, Geotrichum, Metschnikowia, Candida* and *Dipodascus*. A complete list of the genera and the numbers of screened strains from each genus is given in Table 1. All the strains were obtained from the NRLL.

TABLE 1

Genera and number of strains screened

| Genera | # of strains | Genera | # of strains |
|---|---|---|---|
| Debaryomyces | 67 | Lachancea | 1 |
| Geotrichum | 41 | Torulaspora | 1 |
| Metschnikowia | 37 | Naumoria | 1 |
| Candida | 24 | Kodamaea | 1 |
| Dipodascus | 14 | Sugiyamella | 1 |
| Pichia | 5 | Henseniaspora | 1 |
| Trigonopsis | 4 | Cephaloascus | 1 |
| Galactomyces | 4 | Botryozyma | 1 |
| Zygosaccharomyces | 2 | Trichomonascus | 1 |
| Citeromyces | 1 | Sporopachydermia | 1 |
| Saccharomycopsis | 1 | Endomyces | 1 |
| Hyphopichia | 1 | Schizoblastosporion | 1 |
| Wicherhamia | 1 | | |

Media

The medium used for screening had the following composition: 20 g/L glucose, 5 g/L peptone, 3 g/L yeast extract, and 3 g/L malt extract. Agar plates containing the same nutrient composition were used for maintaining the chosen *Debaryomyces hansenii* strains toy regular subculturing. The medium used in the studies of culture condition effects on cell growth and arabitol production of *D. hansenii* SBP-1 had the following composition (per titer of solution): yeast extract, 3 g; $(NH_4)_2SO_4$, 2 g; $K_2HPO_4$, 2.4 g; $KH_2PO_4$, 1.6 g; $MgSO_4.7H_2O$, 1 g; and glycerol 100 g (unless specified otherwise). The medium had an initial pH of 6.7. Glycerol (and other carbon sources used in some studies, i.e., glucose, xylose and sorbitol) was autoclaved separately from other medium components.

Culture Conditions

Typical screening was done at 25° C. with 200-rpm shake speed in 250-ml shake flasks. For cultures that did not grow well at this temperature, a subsequent batch of screening study was done at 30° C. Glycerol and polyol product concentrations in the broths were analyzed after 5 days of cultivation. The studies for culture condition effects with *D. hansenii* SBP-1 were also made with 250-ml flasks shaken at 200 rpm. The temperature used in these studies was 30° C. except in the study of temperature effects. Multiple samples were taken along the cultivation to establish the profiles of cell growth, substrate consumption and product formation.

Inoculum Preparation

To prepare inoculum for each culture condition study, a loop of yeast cells was transferred from an agar plate to a 250-ml Erlenmeyer flask covered with cheese cloth (to allow air exchange without introduction of contaminating organisms or spores). The flask contained 50 ml of the culture medium described in a previous section. The culture was grown at room temperature (22±1° C.) for 24 h under vigorous magnetic stirring. The inoculum thus prepared was added at 5% of the final broth volume in the subsequent culture condition study.

Effect of Medium Volume in Shaker Flasks

Shake flasks are not very suitable for studying the effects of dissolved oxygen concentrations (DO) on ceil growth and product formation. Nonetheless, to obtain a qualitative sense in the culture sensitivity to tow DO or anaerobic conditions, a study was done with *D. hansenii* SBP-1 in 250 ml shake flasks containing different medium volumes: 30, 50, 100 and 150 ml. Under the same shake speed (200 rpm), the flasks with smaller volumes were expected to have better oxygen transfer efficiency via surface aeration, resulting in higher broth DO (for the cultures of similar cell concentrations reached in the N-limited culture medium).

Analytical Methods

Cell Concentration

Cell concentrations were mostly determined from the intracellular protein concentrations measured using the Bradford protein assay kit II (Bio-rad Laboratories, Hercules, Calif.). A 5-ml broth sample was centrifuged at 8,000 rpm for 10 min (Sorvall RC 5c, DuPont, Wilmington, Del.). The supernatant was collected and frozen for future analyses of substrate and product (arabitol) concentrations. The cell pellet was washed twice with de-ionized water and then lysed by addition of 5 ml of 0.2 N NaOH and heating at 100° C. for 20 min. The protein concentration of the lysate was measured according to the Bradford assay, with the absorbance at 595 nm measured using a UV/VIS spectrophotometer (Model UV-1601, Shimadzu Corporation, Columbia, Md.). The relationship between the intracellular protein concentration and the cell dry-weight concentration was established with the samples taken during the exponential growth phase of 2 repeated batch fermentation experiments. The following relationship was obtained ($R^2$=0.92): Cell dry-weight concentration (g/L)=Intracellular protein concentration (g/L)×12.42.

Substrate and Production Concentrations

Glycerol, glucose, xylose, and arabitol concentrations were measured by high performance liquid chromatography (HPLC, Shimadzu) using a carbohydrate column (Supelco column H, 250×4.6 mm, with a guard column, 50×4.8 mm). The column was maintained at ambient temperature. The mobile phase used was 0.1% $H_3PO_4$ at a flow rate of 0.17 ml/min. Sorbitol concentration was analyzed using a Supelcosil LC-$NH_2$ column (250×4.6 mm) with 25:75 acetonitrite: water as the mobile phase at a flow rate of 10 ml/min. Elution peaks for ail the compounds mentioned above were detected by a refractive index defector. Pure standards of known concentrations were used to identify the corresponding peaks and establish the calibration relationships for determination of concentrations in the samples.

Screening for Arabitol Production from Glycerol

Among the cultures screened (Table 1), the genera *Debaryomyces* and *Geotrichum* had the largest numbers of strains that produced noticeable amounts (≥5 g/L) of polyols from glycerol, after 5 days of cultivation in the shake flasks (Table 2).

TABLE 2

Strains producing at least 5 g/L of total polyols, listed in alphabetical and SBP# order

| Species | SBP# | Total polyol, g/l |
|---|---|---|
| Candida quercitrusa | 118 | 6 |
| Debaryomyces hansenii | 1 | 10 |
| D. hansenii | 2 | 11 |
| D. hansenii | 3 | 9 |
| D. hansenii | 5 | 5 |
| D. hansenii | 7 | 5 |
| D. hansenii | 8 | 5 |
| D. hansenii | 15 | 5 |
| D. coudertii | 33 | 5 |
| Galactomyces reesii | 167 | 8 |
| Geotrichum candidum | 12 | 14 |
| G. candidum | 181 | 8 |
| G. candidum | 182 | 5 |
| G. candidum | 188 | 9 |
| G. candidum | 189 | 15 |
| G. cucojoidarum | 194 | 19 |
| G. cucojoidarum | 219 | 13 |
| G. fermentans | 169 | 10 |
| G. fragrans | 177 | 7 |
| G. histeridarum | 195 | 10 |
| G. klebahnii | 197 | 9 |

TABLE 2-continued

Strains producing at least 5 g/L of total polyols,
listed in alphabetical and SBP# order

| Species | SBP# | Total polyol, g/l |
|---|---|---|
| G. silvicola | 199 | 6 |
| Geotrichum sp. | 201 | 8 |
| Geotrichum sp. | 204 | 9 |
| Geotrichum sp. | 210 | 7 |
| Geotrichum sp. | 211 | 9 |
| Geotrichum sp. | 215 | 6 |
| Geotrichum sp. | 216 | 8 |
| G. suaveolens | 217 | 8 |
| G. vulgare | 218 | 8 |
| Metschnikowia zobellii | 14 | 5 |

*Debaryomyces* and *Metschnikowia* strains tended to produce predominantly arabitol whereas *Geotrichum* strains produced amounts of mannitol, in addition to arabitol. Examples for the distribution of different polyols produced are compared in Table 3 for several strains.

TABLE 3

Percentages of different polyols produced by
some osmotolerant yeast strains

| | | Total polyol | Polyol distribution (%) | | | |
|---|---|---|---|---|---|---|
| Species | SBP# | (g/L) | Arabitol | Xylitol | Mannitol | Ribitol |
| Debaryomyces hansenii | 1 | 10 | 97.8 | 1.6 | ND | 0.6 |
| D. hansenii | 2 | 11 | 97.4 | 2.6 | ND | ND |
| Geotrichum candidum | 12 | 14 | 65.3 | 1.0 | 33.7 | ND |
| G. cucujoidarum | 194 | 19 | 59.0 | 0.8 | 39.4 | 0.8 |
| G. cucujoidarum | 219 | 13 | 71.7 | 0.8 | 25.9 | 1.6 |
| Metschnikowia Zobellii | 14 | 5 | 94.9 | ND | ND | 5.1 |

ND: not detectable

Selected strains from these genera, specifically *D. hansenii* (SBP-1), *G. candidum* (SBP-12), *G. cucujoidarum* (SBP219), and *M. zobellii* (SBP-14), were examined further for the effects of some cultivation conditions. More thorough studies were done with *D. hansenii* (SBP-1) because the minimal amount of non-arabitol polyols produced by this strain was expected to significantly simplify the downstream arabitol purificatson process.

Effect of Culture Volume in Shaker Flasks

The different medium volumes (30, 50, 75, 100, and 150 ml) used in the studied systems were supposed to cause different profiles (varying with time) of dissolved oxygen concentrations (DO) in the broth. DO profiles were, however, difficult to follow in shake-flask cultures. Instead, the concentrations of *D. hansenii* SBP-1 cells, arabitol produced and glycerol consumed were compared in FIG. 1 to show the possible effects of DO. The cell concentrations were measured at 80 h because the preliminary study had shown that the cultures would typically have reached the stationary phase by 80 h. Arabitol and glycerol concentrations were measured at 120 h, to allow ample time for arabitol production. The systems with 30, 50 and 75 ml medium were found to have comparable results for all 3 concentrations (cells, arabitol and glycerol). The systems with 100 and 150 ml medium reached lower cell and arabitol concentrations and consumed less glycerol, presumably due to the insufficient oxygen transfer in these larger volume systems. More importantly, the yields of arabitol from consumed glycerol remained about 20% (19%-22%) in the 3 systems with lower volumes but decreased to 10% and 5% as the volume increased to 100 ml and 150 ml, respectively. The results indicated that the 50 ml volume used in the initial screening study was suitable. The same volume was used in all the subsequent shake-flask studies. The results also suggested that very low or zero DO, corresponding to the systems of larger medium volumes, was not good for arabitol production.

Effect of Temperature

Figure 2:
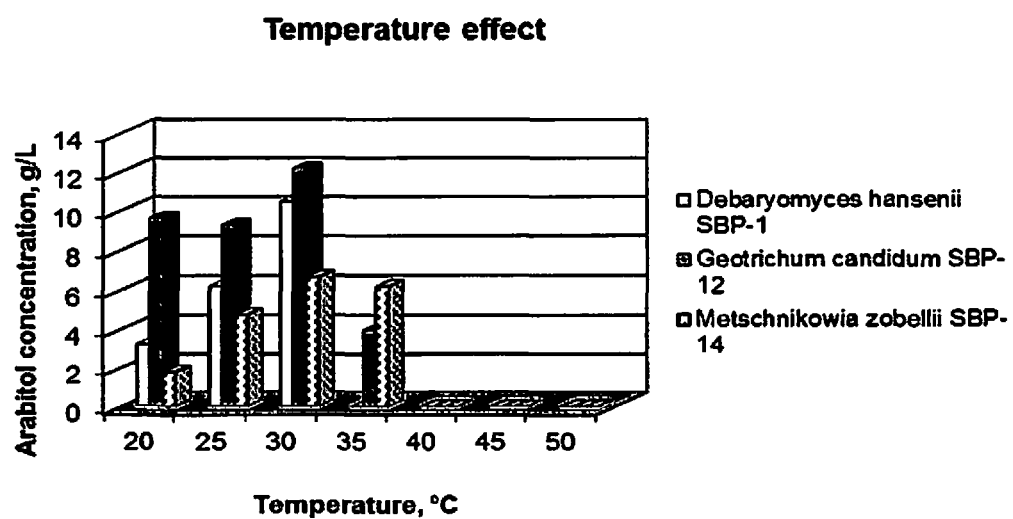
FIG. 2 is a graph illustrating arabitol produced by selected strains of *Debaryomyces, Geotrichum* and *Metschnikowia* at different temperatures; wherein samples were taken after 3 days of cultivation.

The concentrations of arabitol produced at different temperatures by *D. hansenii* (SBP-1), *G. candidum* (SBP-12) and *M. zobellii* (SBP-14), after 3 days of cultivation, were compared in FIG. 2. All of these strains showed maximal arabitol production at 30° C. *D. hansenii* (SBP-1) was found particularly sensitive to higher temperature, giving negligible arabitol production at 35° C. Arabitol production by *M. zobellii* (SBP-14) was, on the other hand, similar at 30° C. and 35° C.

Effect of Initial Glycerol Concentration

Figure 3:
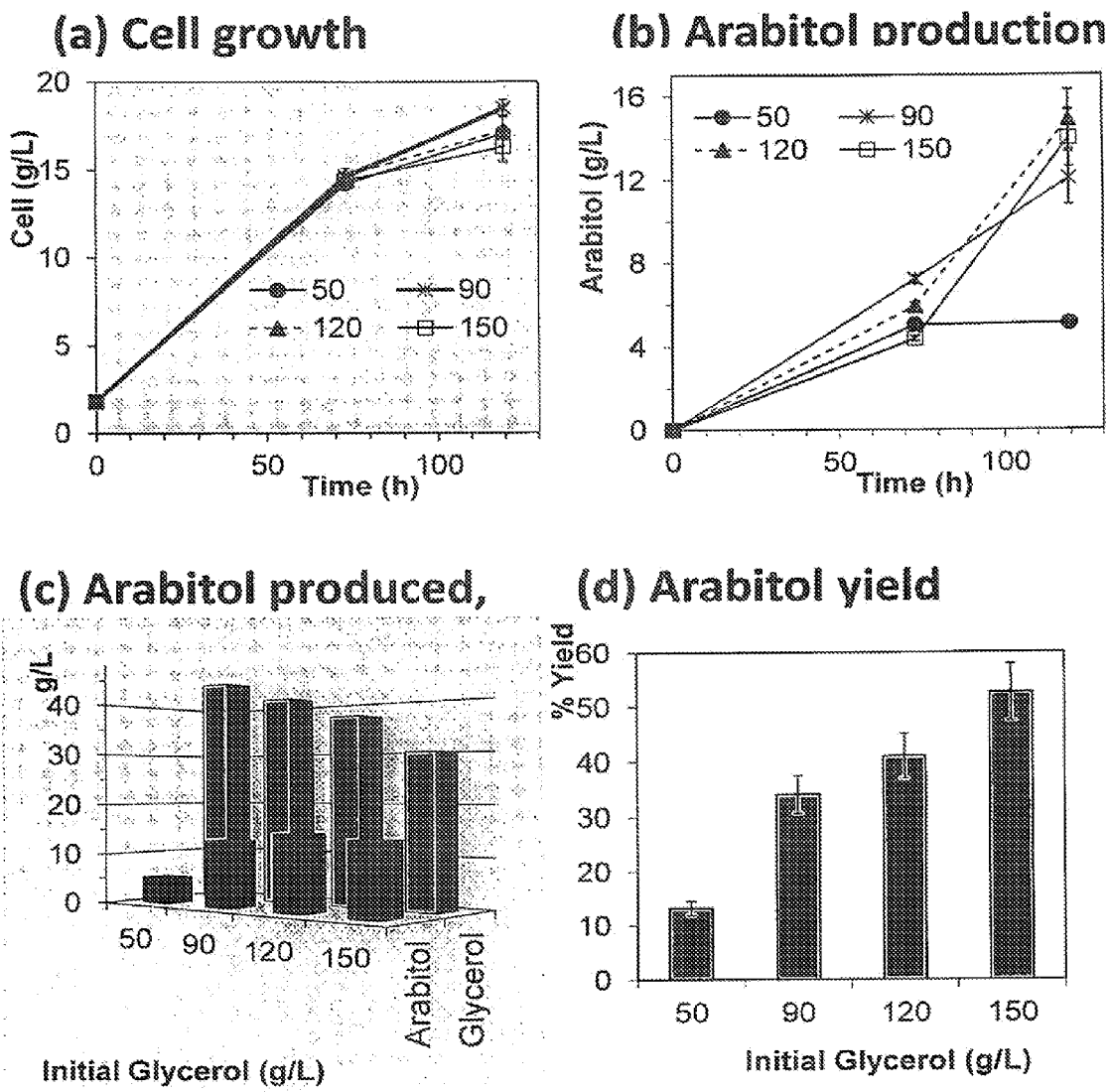
FIGS. 3(*a*)-(*d*) are graphs illustrating effects of different initial glycerol concentrations on *D. hansenii* fermentation, wherein (*a*) shows cell growth profiles, (*b*) shows arabitol production profiles, (*c*) shows concentrations of glycerol consumed and arabitol produced at 120 h, and (*d*) shows arabitol yield from consumed glycerol) at 120 h.

Arabitol production is associated with the osmophilic nature of the yeast cultures (Blakley and Spencer 1962). The effects of glycerol and salt concentrations, both can present osmotic pressure to the cells, are described in this and the next sections, respectively. Shown in FIG. 3(*a*) are the cell concentrations of *D. hansenii* SBP-1 at 0, 72, and 120 h in the systems with 50, 90, 120 and 150 g/L of glycerol in the initial media. The ceil concentrations were comparable, reaching 17-20 g/L, presumably because all were limited by the same N-source concentration in the media. Glycerol was not completely exhausted in any systems at 120 h (glycerol concentration data not shown). The profiles of arabitol production in these systems are shown in FIG. 3(*b*). In the system with 50 g/L glycerol initially, the arabitol production essentially stopped after 72 h (when the remaining glycerol concentration dropped below 20 g/L). Arabitol production continued after 72 h in the systems with higher initial glycerol concentrations. The concentrations of arabitol produced and glycerol consumed at 120 h are summarized in FIG. 3(*c*). The arabitol production in the 3 systems with high initial glycerol concentrations (≥90 g/L) appeared to be comparable whereas the glycerol consumption decreased with increasing initial glycerol concentrations. The resultant arabitol yields from the consumed glycerol at 120 h were shown in FIG. 3(*d*). The arabitol yield increased with the increase in initial glycerol concentration, particularly from 50 g/L to 90 g/L. The arabitol yield reached about 50% in the system with 160 g/L of initial glycerol. The findings suggested that certain glycerol concentration (and/or its associated osmotic pressure) was required for arabitol synthesis by the osmophilic yeast.

Effect of Salt Concentration

The above results also indicated that certain concentrations of glycerol would remain unconsumed when the arabitol production by *D. hansenii* SBP-1 became very slow or stopped. The remaining glycerol would complicate the downstream collection and purification of arabitol, it was thought that sail (NaCl) might be able to offer the necessary osmotic stress for complete conversion of glycerol to arabitol. *D. hansenii* was reported to tolerate high salt concentrations, up to 4M NaCl (Larsson et al. 1990).

Figure 4:
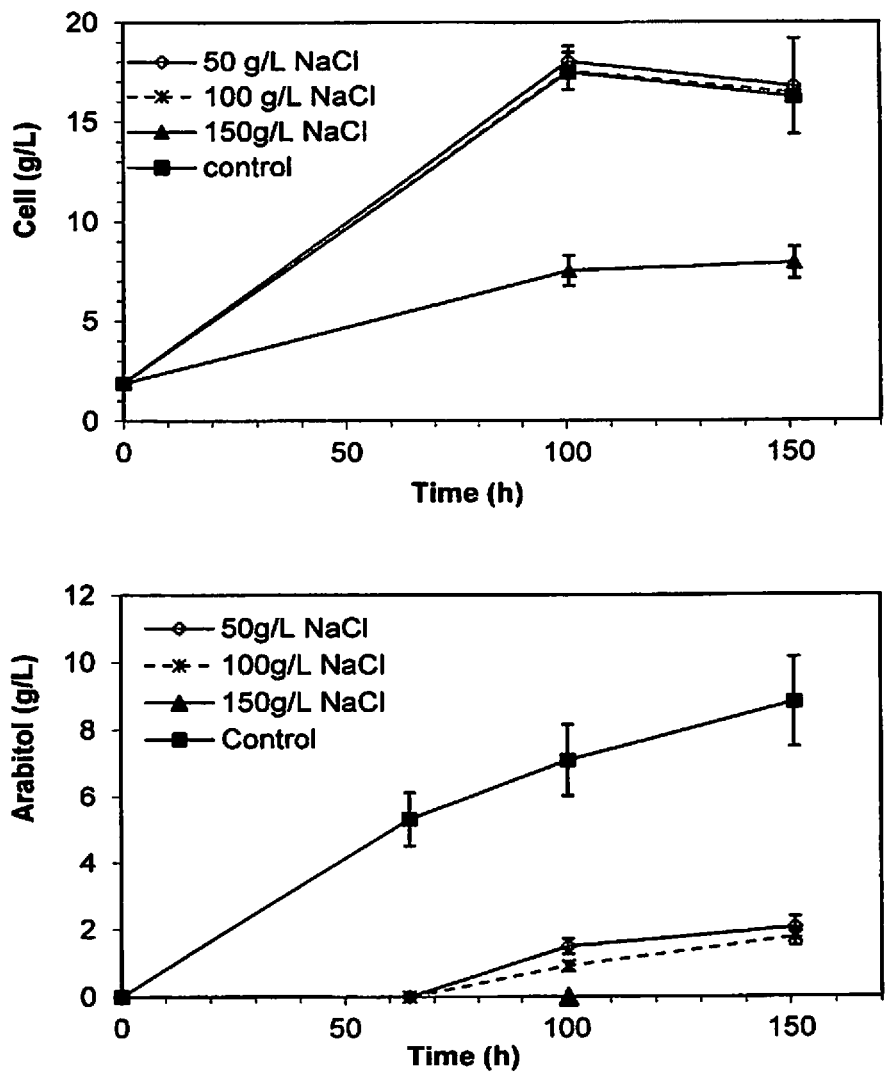
FIGS. 4(*a*) and (*b*) are graphs illustrating effects of different salt concentrations on *D. hansenii* fermentation with 100 g/L of initial glycerol concentration, wherein (*a*) shows cell growth and (*b*) shows arabitol production profiles.
Figure 5:
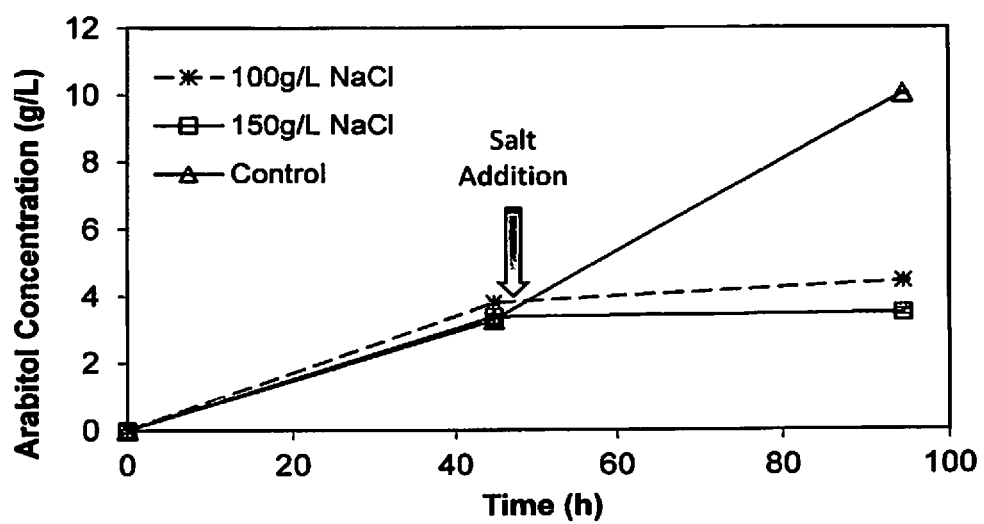
FIG. 5 is a graph illustrating effects of salt addition on arabitol production by *D. hansenii* in media with 100 g/L of initial glycerol concentration, wherein the salt was added after 2 days of growth.

The study was made in media containing 100 g/L of glycerol and 0, 50, 100 and 150 g/L of NaCl, respectively. The cell growth was not affected by addition of 50 and 100 g/L NaCl but was slowed down significantly in the system with 150 g/L NaCl (FIG. 4). Arabitol production was more sensitive to the salt addition (FIG. 4). Presence of even 50 g/L NaCl caused significantly poorer arabitol production. The system with 150 g/L NaCl produced less than 1 g/L of arabitol. To separate the effect of NaCl addition on arabitol production from that on cell growth, a subsequent study was made with the salt being added after 2 days of cell growth in the medium with 100 g/L glycerol. Three systems, with 0 (control), 100 and 150 g/L NaCl, respectively, were included for comparison. Delaying the salt addition successfully minimized the negative effect on cell growth (data not shown). Arabitol production was, however, completely stopped after the salt addition (FIG. 5). It is therefore concluded that high salt concentrations have negative effects on arabitol production by *D. hansenii* SBP-1. It is infeasible to use salt addition to apply osmotic pressure for complete conversion of glycerol to arabitol.

Effects of NaCl addition (25, 50 and 100 g/L) on arabitol production were also evaluated with other strains, including *D. hansenii* SBP-2 and SBP-5, *G. candidum* SBP-12, and *G. cucujoidarum* SBP-194 and SBP-219. Salt addition was found to have similar negative effects on arabitol production by these strains (data not shown).

Effects of Addition of Other Carbon Substrates

Figure 6:
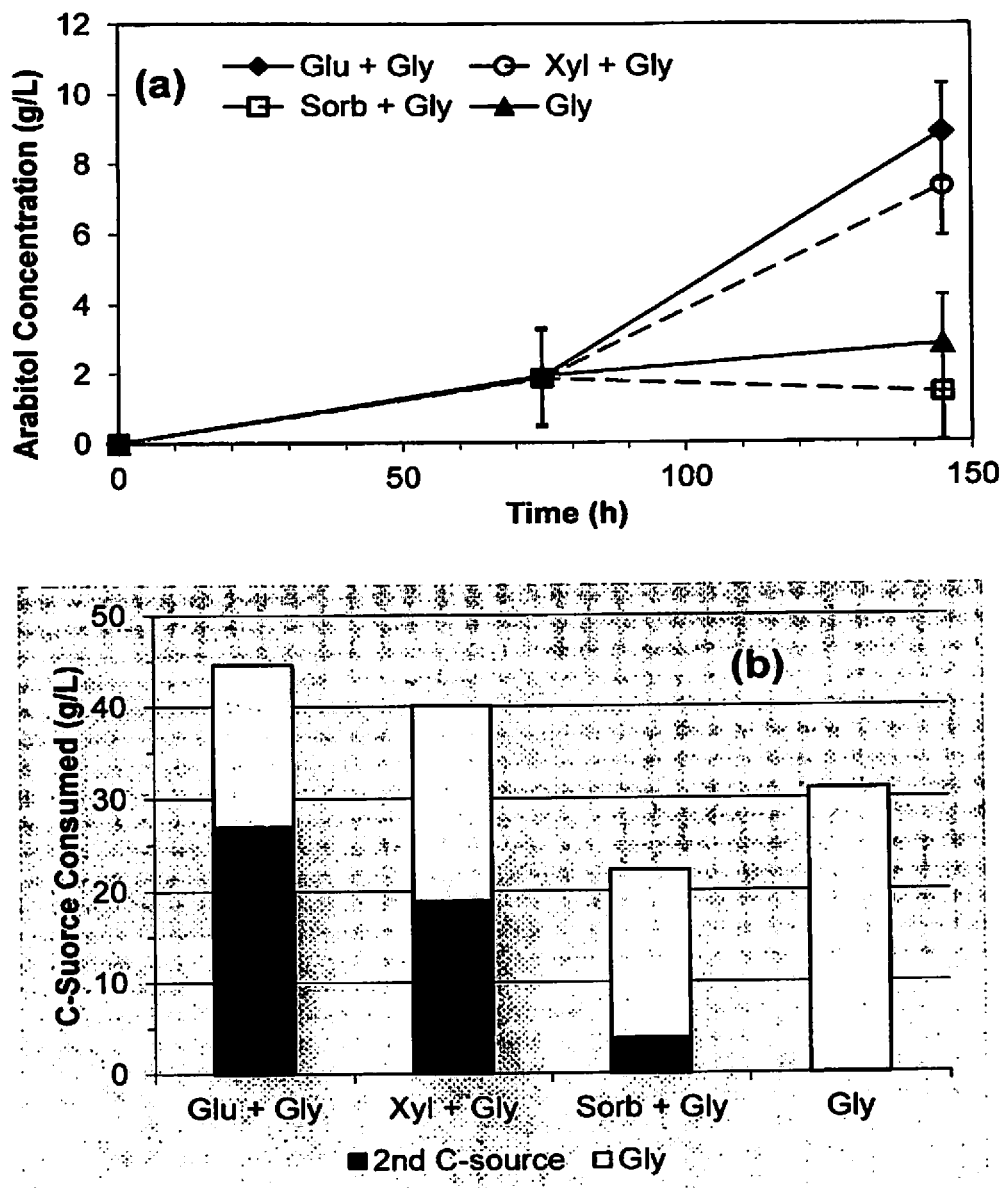
FIGS. 6(*a*) and (*b*) are graphs illustrating effects of addition of 30 g/L glucose, xylose or sorbitol as a potential second carbon source, along with 50 g/L glycerol, on arabitol production by stationary-phase *D. hansenii*, wherein cells were grown for 74 h in media containing 30 g/L, i.e. glycerol, arabitol production profiles are compared in (*a*), concentrations of the second C-source and glycerol consumed by the stationary-phase cultures (during 74-145 h) are shown in (*b*), and although not shown, the standard deviations of the consumed concentrations in (*b*) were in range of 13% to 22%.

The effects of addition of glucose, xylose, and sorbitol, along with glycerol, on arabitol production by *D. hansenii* SBP-1 were investigated in 4 systems. The study was made by first growing the culture in the medium with an initial-glycerol concentration of 30 g/L. After 74 h (when the cultures were in the early stationary phase), 30 g/L glucose, xylose, or sorbitol plus 50 g/L glycerol were added to 3 of the systems, and 80 giL glycerol was added to the 4th (control) system. All of the systems reached similar maximum cell concentrations (about 16 g/L, data not shown). The resultant arabitol concentration profiles are shown in FIG. 6(a). Before the addition of more carbon substrates at 74 h, all of the systems produced about 2 g/L arabitol. The subsequent addition of 80 g/L glycerol (in the control system) did not lead to much more arabitol production (FIG. 6(a)). Such a two-step addition of glycerol (30 g/L and then 80 g/L) appeared to be less favorable for arabitol production, when compared to the addition of all the glycerol in the initial medium (see the arabitol profiles for the systems with 90 g/L and 120 g/L of initial glycerol concentrations in FIG. 3(b) and the profiles for the control systems in FIGS. 4 and 5). The addition of sorbitol along with glycerol also did not give good arabitol production (FIG. 8(a)). On the other hand, additions of glucose and xylose significantly improved the arabitol production. Concentrations of the potential second C-source (glucose, xylose or sorbitol) and glycerol consumed after the addition in the stationary phase (during 74-145 h) are summarized in FIG. 6(b). More glycerol was consumed in the control system (added with only glycerol) than in the other 3 systems. Sorbitol was not consumed much. The lower glycerol consumption in this system might be caused by the lower added glycerol concentration (50 g/L, as compared to 80 g/L in the control) or by the inhibition of sorbitol. On the other hand, glucose and xylose were simultaneously or preferentially consumed by the yeast. It should also be noted that arabitol remained the only major metabolite detected in all of the systems. Addition of these other carbon substrates did not shift the culture metabolism to synthesize other major metabolites.

The experiments conducted showed that the species from different genera produced different polyols or polyol mixtures from glycerol. High initial glycerol concentrations (≥90 g/L) were found to be favorable for arabitol production and yield. High salt concentrations, on the other hand, tended to inhibit yeast growth and, particularly, arabitol production. Cell growth was affected at salt concentrations higher than 100 g/L; arabitol production was inhibited even at 50 g/L NaCl.

Arabitol production was found to be improved by addition of glucose and xylose, but not sorbitol. Arabitol is synthesized via the pentose phosphate pathways (Saba et al. 2007). The possible routes are summarized in FIG. 7.

Ribulose-5-phosphate is considered as an important precursor for production of polyols like arabitol, xylitol and erythritol (Bernard et al.). With glucose as the substrate, two routes were reported for *Zygosaccharomyces rouxii* (Saba et al. 2007) and *S. rouxii* (Ingram and Wood 1965) (Blakley and Spencer 1962b). Glucose is converted to ribulose 5-phosphate, which is then converted either to ribulose by ribulokinasae or to xylulose 5-phosphate by ribulose 5-phosphate epimerase. Ribulose is reduced to arabitol by an NADPH-dependent arabitol dehydrogenase. Xylulose 5-phosphate is dephosphorylated to xylulose by xylulokinase and then reduced to arabitol by an NADH-dependent arabitol dehydrogenase.

Figure 7:
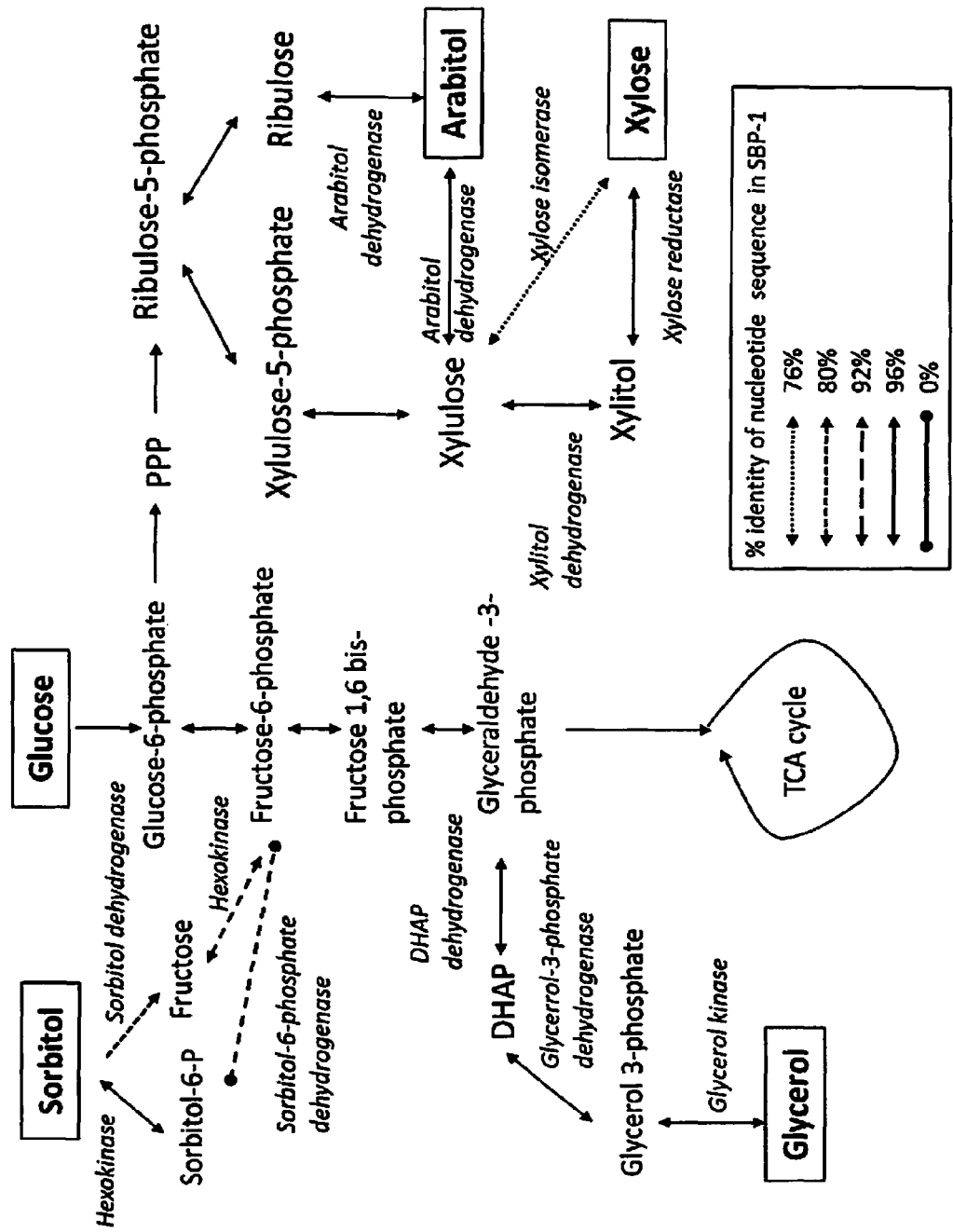
FIG. 7 is schematically illustrates possible pathways for the conversion of various substrates to arabitol.

Arabitol synthesis from xylose also may follow two possible ways, see FIG. 7, as reported in the studies with *Z. rouxii* and *Aerobacter aerogenes* (Wilson and Mortlock 1973; Saha et al. 2007). In the first route xylose is reduced to xylitol and then to xylulose. In the second route xylose is directly converted to xylulose by xylose isomerase. Xylulose is then reduced to arabitol by arabitol dehydrogenase.

Arabitol syntheses from sorbitol and glycerol, if occurring, are expected to follow similar routes as glucose after they are converted to glucose-6-phosphate, see FIG. 7. Sorbitol is first converted to fructose-8-phosphate via fructose or sorbitol-6-phosphate. Fructose-6-phosphate is then converted to glucose-6-phosphate. As for glycerol, the metabolic pathway in yeasts like *Candida utilis* and *Saccharomyces cerevisiae* is initiated by glycerol kinase and a mitochondrial sn-glycerol 3-phosphate dehydrogenase (Gancedo C 1968). An alternative pathway in yeasts lacking glycerol kinase is indicated by the presence of NAD-dependent glycerol dehydrogenase and dihydroxyacetone kinase (Babel and Hofmann 1982). Dihydroxyacetone phosphate, formed in the above routes, is converted to glyceraldehyde-3-phosphate and, subsequently via gluconeogenesis pathway, to glucose-6-phosphate. *C. utilis* was reported to utilize glycerol faster than *S. cerevisiae* (Gancedo C 1968). There seems to be no reports on the uptake transport system of glycerol in *C. utilis*, although glycerol transport by simple diffusion was described for *S. cerevisiae* (Lages and Lucas 1997).

The nucleotide sequences for the relevant enzymes reported have been searched and compared with the *D. hansenii* genome (NC 006048) using the NCBI-BLAST (National Center for Biotechnology information-Basic Local Alignment Search Tool). The matching percentages are indicated in FIG. 7 by different arrow styles. Sorbitol conversion to fructose-6-phosphate is noticeably less certain, consistent with the insignificant sorbitol utilization observed in this study, see FIG. 8(b).

Arabitol Production from Glucose and Xylose as Carbon Sources

Figure 8:
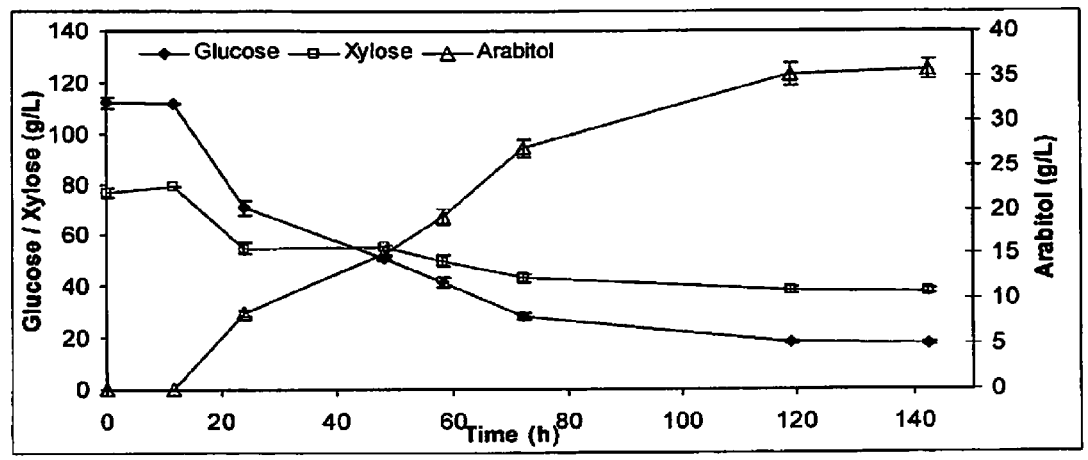
FIG. 8 is a graph illustrating glucose and xylose consumption and arabitol production over time.

Glucose and xylose are the major carbon sources present in hydrolysate of plant biomass. An experiment was conducted to study arabitol production with glucose and xylose as carbon sources instead of glycerol. The ratio of glucose to xylose was kept the same as that in the hydrolysate. 35 grams of arabitol per liter of medium was produced with 110 g/L of glucose and 80 g/L of xylose initially in the medium. FIG. 8 shows the consumption of the carbon sources present in the medium (glucose and xylose) and arabitol production profile over this time.

Effect of Dissolved Oxygen Concentration on Arabitol Production

Figure 9:
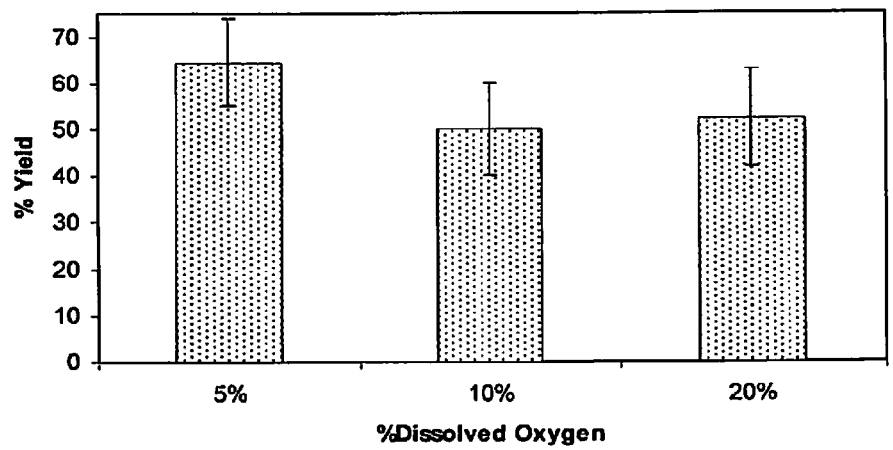
FIG. 9 is a graph illustrating arabitol yield at different dissolved oxygen concentrations.

The following results were performed in a 2 L fermenter with 1 L working volume. In these fermentation runs, glycerol was used as carbon source. Low dissolved oxygen concentrations of 5% showed about 60% yield of arabitol based on total glycerol consumed. More aerobic conditions with dissolved oxygen concentrations above 5% were also good for cell growth rate and 5% dissolved oxygen was good for arabitol production. FIG. 9 shows total arabitol yield for 5, 10, and 20% dissolved oxygen concentrations.

Accordingly, methods for producing arabitol in particular from a mixture including a carbon source such as glycerol or glucose and xylose have been described. Biodiesel byproduct glycerol can be utilized as the substrate for arabitol production in a preferred embodiment. Arabitol has many uses, including as a low calorie sweetener.

While in accordance with the patent statutes the best mode and preferred embodiment have been set forth, the scope of the invention is not limited thereto, but rather by the scope of the attached claims.

What is claimed is:

1. A process for producing arabitol, comprising the steps of;
   combining a carbon source with an osmophilic yeast in a medium, forming a medium mixture, the yeast being one or more of the genera *Debaryomyces* and *Metschnikowia*; and
   producing greater than 60 parts by weight of the arabitol based on 100 total parts by weight of all polyols produced by the process, and wherein the arabitol is produced in a concentration greater than 30 g/L of the medium and with at least 40% conversion of the carbon source consumed;
   wherein the concentration of dissolved oxygen in the medium mixture is less than 20%.

2. The process according to claim 1, wherein the concentration of dissolved oxygen in the medium mixture is in the range of from 5% to 20%.

3. The process according to claim 1, wherein the carbon source is one or more of glycerol, glucose, xylose and a hydrolysate of lignocellulosic biomass.

4. The process according to claim 3, further comprising the step of obtaining the glycerol as a byproduct from biodiesel production.

5. The process according to claim 1, wherein the yeast is one or more of *D. hansenii* and *M. zobellii*.

6. The process according to claim 3, wherein at least glycerol is used as the carbon source, wherein the concentration of the glycerol in the initial mixture is from about 50 to about 400 g/L of the medium, wherein concentration of the yeast in the initial mixture is from about 0.05 to about 5 g/L of the medium, wherein the arabitol is produced in an amount greater than 60 parts by weight based on 100 total parts by weight of polyol, and wherein the arabitol is produced in an amount greater than 35 g/L of medium.

7. The process according to claim 6, wherein the production of arabitol is carried out at a temperature in a range between about 20° C. to about 50° C., wherein the pH of the mixture is from about 3 to about 6, and wherein the mixture further includes one or more of following nitrogen sources: from about 3 to about 30 grams of yeast extract, from about 2 to about 20 grams of ammonium sulfate, from about 3 to about 30 grams of peptone, and from about 3 to about 50 grams of malt extract, all per liter of medium.

8. The process according to claim 6, further including the step of carrying out the production under aerobic conditions, wherein the arabitol is produced in an amount greater than 90 parts by weight based on 100 total parts by weight of polyol, and wherein the arabitol is produced in an amount greater than 50 g/L of medium.

9. The process according to claim 6, wherein the carbon source further includes one or more of glucose, xylose, and hydrolysate of lignocellulosic biomass.

10. The process according to claim 1, wherein the medium has a pH in a range of from 3 to 6.

11. A process for producing arabitol, comprising the steps of:
    combining a carbon source with an osmophilic yeast in a medium, forming a medium mixture, the yeast being of one or more of the genera *Geotrichum*; and
    producing greater than 60 parts by weight of the arabitol based on 100 total parts by weight of all polyols produced by the process, and wherein the arabitol is produced in a concentration greater than 30 g/L of the medium and with at least 40% conversion of the carbon source consumed;
    wherein the concentration of dissolved oxygen in the medium mixture is less than 20%.

12. The process according to claim 1 further comprising the step of identifying a yeast species that is capable of producing greater than 60 parts by weight arabitol, less than 10 parts by weight xylitol, less than 40 parts by weight mannitol, and less than 10 parts by weight ribitol, each based on 100 total parts by weight of all polyols produced by the yeast species, where said identifying step is based on a previous culture screening of the yeast species, where said identifying step occurs before said combining step.

13. The process according to claim 1, wherein the concentration of dissolved oxygen in the medium mixture is in the range of from 5% to 10%.

* * * * *

UNITED STATES PATENT AND TRADEMARK OFFICE
CERTIFICATE OF CORRECTION

| | | |
|---|---|---|
| PATENT NO. | : 9,062,329 B2 | Page 1 of 1 |
| APPLICATION NO. | : 13/811298 | |
| DATED | : June 23, 2015 | |
| INVENTOR(S) | : Ju | |

It is certified that error appears in the above-identified patent and that said Letters Patent is hereby corrected as shown below:

Title Page

Item (54) Title and in the specification at column 1, line 1, delete "ARABITAL" and insert --ARABITOL--.

Signed and Sealed this
Twelfth Day of April, 2016

Michelle K. Lee
*Director of the United States Patent and Trademark Office*